United States Patent [19]

Prossel et al.

[11] 4,246,403
[45] Jan. 20, 1981

[54] 1,3,4-OXADIAZOLONE-(2) COMPOUNDS AND PROCESS FOR THEIR MANUFACTURE

[75] Inventors: Günter Prossel, Burgkirchen; Erich Schinzel, Hofheim am Taunus; Norbert Schönberger, Kelkheim; Thomas Martini; Günter Rösch, both of Bad Soden am Taunus, all of Fed. Rep. of Germany

[73] Assignee: Hoechst Aktiengesellschaft, Fed. Rep. of Germany

[21] Appl. No.: 60,823

[22] Filed: Jul. 25, 1979

[30] Foreign Application Priority Data

Jul. 29, 1978 [DE] Fed. Rep. of Germany ....... 2833470

[51] Int. Cl.³ ................. C07D 271/10; C07D 413/10; C07D 413/14
[52] U.S. Cl. ..................................... 542/432; 542/442; 542/443; 542/444; 542/454; 542/456; 542/458; 542/459; 542/136; 548/144
[58] Field of Search ............... 542/442, 443, 444, 454, 542/456, 458, 459, 464, 432, 436; 548/144

[56] References Cited

U.S. PATENT DOCUMENTS

| | | | |
|---|---|---|---|
| 3,635,960 | 1/1972 | DiGiouandel et al. | 542/456 |
| 3,732,221 | 5/1973 | Siegrist et al. | 542/459 |
| 3,984,399 | 10/1976 | Weber et al. | 542/459 |
| 4,088,762 | 5/1978 | Hakim et al. | 542/444 |
| 4,150,142 | 4/1979 | Boesch | 548/144 |
| 4,166,176 | 8/1979 | Eckstein et al. | 542/456 |

OTHER PUBLICATIONS

Elderfield Heterocyclic Compounds vol. 7, John Wiley & Sons, N. Y., N. Y., 1962 p. 528–529.

*Primary Examiner*—Arthur P. Demers
*Attorney, Agent, or Firm*—Connolly and Hutz

[57] ABSTRACT

Novel 1,3,4-oxadiazolone-(2) compounds of the formula

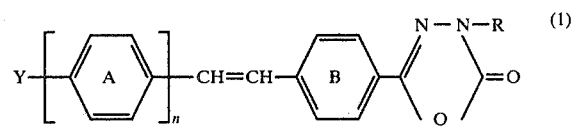

wherein Y denotes carboxy optionally functionally modified or optionally substituted phenyl or a five-membered heterocycle optionally substituted and selected from the group consisting of: furan, thiophen, oxazole, imidazole, oxadiazole, oxadiazolone, triazole, benzofuran, thionaphthalene, benzoxazole, benzimidazole, and benzotriazole, R denotes hydrogen, alkyl or optionally substituted phenyl, n denotes 0 and 1 and the rings A and B carry optionally further non-chromophoric substituents. These compounds may be used as optical brighteners.

2 Claims, No Drawings

1,3,4-OXADIAZOLONE-(2) COMPOUNDS AND PROCESS FOR THEIR MANUFACTURE

The present invention relates to novel 1,3,4-oxadiazolone-(2) compounds of the formula

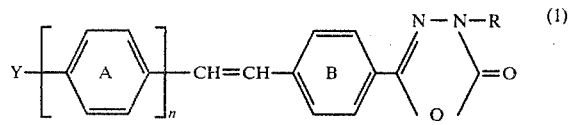

wherein
- Y denotes carboxy optionally functionally modified or optionally substituted phenyl or a five-membered heterocycle optionally substituted and selected from the group consisting of: furan, thiophen, oxazole, imidazole, oxadiazole, oxadiazolone, triazole, benzofuran, thionaphthalene, benzoxazole, benzimidazole, and benzotriazole,
- R denotes hydrogen, alkyl or optionally substituted phenyl, n denotes 0 and 1 and
- the rings A and B carry optionally further non-chromophoric substituents.

As non-chromophoric substituents of the rings A and B there may be mentioned, in particular: alkyl having of from 1 to 12 carbon atoms, cyclohexyl, phenylalkyl having of from 1 to 13 carbon atoms in the alkyl moiety, unsubstituted phenyl or phenyl substituted by 1 or 2 substituents selected from the group consisting of chlorine, methyl or methoxy; alkoxy having of from 1 to 4 carbon atoms; unsubstituted phenoxy or phenyl substituted by 1 or 2 substituents selected from the group consisting of chlorine, methyl or methoxy; chlorine; fluorine; bromine; cyano; —COOY with Y being hydrogen, a salt-forming cation, alkyl having of from 1 to 15 carbon atoms or benzyl; —CONY'($Y_1'$) with Y' being hydrogen, alkyl having of from 1 to 6 carbon atoms, hydroxyalkyl having of from 1 to 4 carbon atoms, alkoxyalkyl having of from 2 to 8 carbon atoms, phenyl or benzyl and $Y_1'$ being hydrogen, alkyl having of from 1 to 6 carbon atoms, hydroxyalkyl having of from 1 to 4 carbon atoms or alkoxyalkyl having of from 2 to 8 carbon atoms or Y' and $Y_1'$, when taken together, forming together with the nitrogen atom a morpholino or piperidino radical; modified sulfo such as —$SO_2OY$ with Y being defined as above; —$SO_2NY'(Y_1')$ with Y' and $Y_1'$ being as defined above; alkylsulfonyl having of from 1 to 6 carbon atoms; benzylsulfonyl or unsubstituted phenylsulfonyl or phenylsulfonyl substituted by chlorine or methyl; or, in the case of two substituents in the ortho-position, alkylene having of from 3 to 4 carbon atoms or 1,3-butadienylene.

Preference is given to compounds of the formula (2)

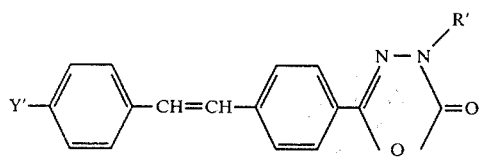

wherein
- Y' denotes phenyl, p-cyanophenyl, p-carbalkoxyphenyl, cyano, carboalkoxy or carbonamide or 5-aryl-1,3,4-oxadiazolyl-(2), 3-aryl-1,3,4-oxadiazol-2-on-yl-(5), 1,2,4-triazolyl-(1), 1,2,3-triazolyl-(2), benzofuranyl-(2), benzoxazolyl-(2), benzimidazolyl-(2), 1,2,4-triazolium or benzimidazolium and
- R' is as defined above or to compounds of the formula

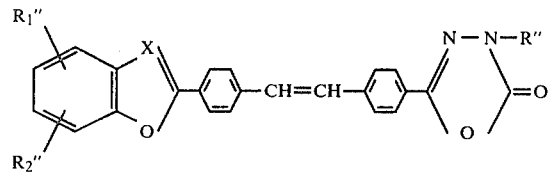

wherein
- X denotes CH or N,
- R" denotes hydrogen or alkyl, optionally substituted by hydroxy, cyano, carboalkyl or alkoxy, halogen, preferably chlorine, dialkylamino or trialkylammonium; phenyl optionally substituted by 1 to 3 alkyl or alkoxy groups or by halogen atoms, preferably fluorine or chlorine or by carboxy optionally functionally modified; and
- $R_1''$ and $R_2''$ independent from one another have the same meaning as R" and additionally may denote alkoxy, halogen, preferably chlorine or fluorine, dialkylamino or trialkylammonium or
- $R_1''$ and $R_2''$ denote, when taken together, dioxymethylene, dioxyethylene, alkylene or butadienylene.

By "alkyl" and groups derived therefrom such as alkoxy or alkylene there are to be understood, unless stated otherwise, groups having of from 1 to 4 carbon atoms. "Functionally modified carboxy groups" include the following groups: CN, COOR and $CONR_2$ wherein R is $C_{1-4}$alkyl and the salts of the carboxy group.

A preferred method of preparing the 1,3,4-oxadiazolone-(2) compounds consists in reacting acid hydrazides of the formula

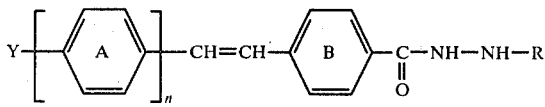

wherein Y, A, B, n and R are as defined above, in an inert solvent in the presence of an acid scavenger with phosgene or chloroformates at a temperature of from about 80° to 150° C.

A further method of preparing the claimed 1,3,4-oxadiazolone-(2) compounds consists in reacting in an inert solvent a compound of the formula

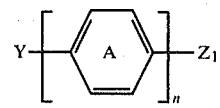

with a compound of the formula

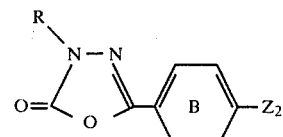

in the presence of an alkaline condensation agent, in the above formulae Y, R, A, B and n being as defined in formula I and one of the symbols $Z_1$ and $Z_2$ denoting formyl and the other one denoting a grouping of the formula

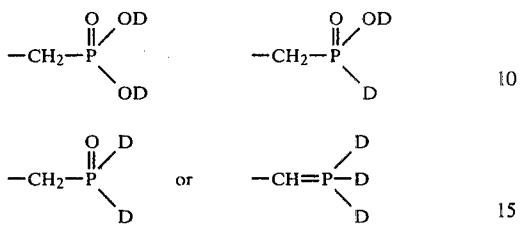

wherein D is unsubstituted or substituted alkyl; aryl; cycloalkyl or aralkyl.

This method of preparation is preferably carried out in inert solvents. Examples of solvents of this type are: hydrocarbons such as toluene and xylene or alcohols such as methanol, ethanol, isopropanol, butanol, glycols, glycol ethers such as 2-methoxyethanol, hexanols, cyclohexanol and cyclooctanol, ethers such as diisopropyl ether, tetrahydrofuran and dioxan or dimethylsulfoxide, formamide and N-methylpyrrolidone. Particularly appropriate are polar organic solvents such as dimethylformamide and dimethylsulfoxide.

The temperature at which the reaction may be performed may vary within wide limits. It depends on the resistance of the solvent used to the reactants, in particular to highly basic alkali metal compounds, on the reactivity of the condensation partners and on the efficiency of the combination solvent-base as condensation agent.

In practice temperatures of from about 10° to 100° C. are generally chosen for the intended purpose, in particular when the solvent used is dimethylformamide or dimethylsulfoxide. The preferred temperature range is between 20° and 60° C.

As highly basic alkali metal compounds there may be mentioned in particular hydroxides, amides and alcoholates (preferably those of primary alcohols containing 1 to 4 carbon atoms) of alkali metals, alkali metal compounds of lithium, sodium and potassium being of particular interest for economical reasons. On principle and in particular cases alkali metal sulfides and carbonates, aryl alkali metal compounds such as phenyl-lithium or highly basic amines, inclusive of ammonium bases, such as trialkylammonium hydroxides, may be used alternatively.

A further process for the manufacture of the 1,3,4-oxadiazolone-(2) compounds according to the invention consists in reacting in a polar, neutral to basic solvent and in the presence of a highly basic alkali metal compound, a Schiff's base of the formula

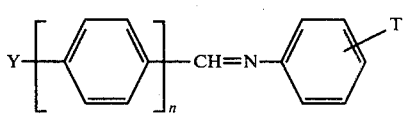

wherein Y, A and n are as defined above and T denotes hydrogen or chlorine, with a methyl compound of the formula

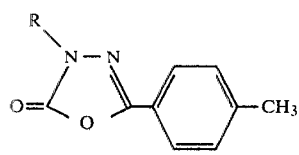

or reacting a Schiff's base of the formula

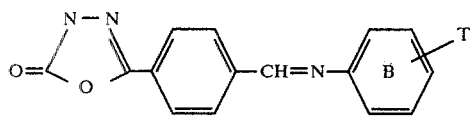

with a methyl compound of the formula

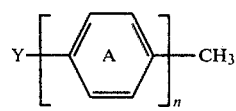

wherein the symbols Y, A, B, R and n are as defined above and T denotes hydrogen or chlorine.

The methyl group-containing compounds may be reacted with the anils in the presence of a suitable highly polar, neutral to alkaline organic solvent, in particular a solvent free from those hydrogen atoms that may be replaced by alkali metals.

In practice, these solvents may be in particular dialkylamides of formic acid and of phosphoric acid or tetraalkylureas, "alkyl" defining a lower alkyl group containing 1 to 4 carbon atoms, in particular methyl. Preference is given to diethylformamide, hexamethylphosphoric acid triamide, tetramethylurea and in particular to dimethylformamide. Mixtures of solvents may likewise be used.

The reaction furthermore requires, as mentioned above, a highly basic alkali metal compound. This compound depends on the nature of the solvent used and on the reactivity of the anil used. Defined sodium alcoholates such as sodium-t-butylate and in particular potassium compounds of the composition $KOC_{m-1}H_{2m-1}$ wherein m is an integer of from 1 to 6, preferably 1 to 5, such as potassium hydroxide or in particular potassium-tert.butylate may be used suitably. When using alkali metal alcoholates, operation may be carried out in practically anhydrous medium, and when using potassium hydroxide a low water content up to about 15% (for example crystal water content) is still acceptable. In some cases potassium hydroxide and sodium-t-butylate should be used suitably in combination with hexamethylphosphoric acid triamide at elevated temperature, for example at 100° to 130° C. Naturally mixtures of various bases may be used as well.

The novel compounds as defined above exhibit a more or less pronounced fluorescence in a dissolved or finely dispersed state. They are therefore suitable for the optical brightening of a great variety of synthetic, semi-synthetic or natural organic materials or substances which contain these organic materials.

Hereinafter there are listed, by way of example only, and without intending to restrict the scope of the invention in any way to the following survey, those groups of organic materials which may be optically brightened:

I. Synthetic organic high molecular materials (a) Polymerization products based on organic compounds containing at least one polymerizable hydrocarbon-hydrocarbon double bond, i.e. homo- or copolymers thereof and aftertreatment products thereof such as cross-linked products, graft products or decomposition products, mixtures of polymers or products obtained by modification of reactive groups, for example polymers based on, β-unsaturated carboxylic acids or on derivatives of these acids, in particular of acrylic compounds such as acrylic esters, accrylic acid, acrylonitrile, acrylamides and derivatives thereof or methacrylic analogous compounds thereof; on olefin-hydrocarbons such as ethylene, propylene, sytrenes or dienes, or so-called ABS-polymers; polymers based on vinyl and vinylidene compounds such as vinyl chloride, vinyl alcohol, vinylidene chloride.

(b) Polymerization products obtainable by ring opening, for example polyamides of the polycaprolactam type, or polymers obtainable both by polyaddition or by polycondensation such as polyethers or polyacetals.

(c) Polycondensation products or precondensates based on bi- or polyfunctional compounds containing groups that are capable of being condensed, homo- and co- condensation products thereof or products obtained in the aftertreatment such as polyesters, in particular saturated, for example ethylene glycol terephthalic acid polyesters, or unsaturated, for example maleic acid dialcohol polycondensates or cross-linked products thereof having vinyl monomers that may be added by polymerization, unbranched or branched polyesters, those based on polyvalent alcohols such as alkyd resins, included, polyamides, for example hexamethylene diamine-adipate, maleinate resins, melamin resins, precondensates and analogous compounds thereof, polycarbonates, silicones.

(d) Polyaddition products such as polyurethanes, which may be cross-linked or non-cross-linked, epoxide resins.

II. Semi-synthetic organic materials, for example cellulose esters having various esterification degrees (the so-called 2½ acetate, triacetate) or cellulose ethers, regenerated cellulose (viscose, copper ammonia cellulose) or aftertreatment products thereof, casein plastics.

III. Natural organic materials of animal or vegetable origin, for example based on cellulose or proteins such as cotton, wool, linen, silks, natural lacquer resins, starch, casein.

The organic materials to be optically brightened may be present in various states of processing, for example as crude products, semi-finished or finished products. They may moreover have a great variety of shape, i.e. mainly three-dimensional bodies such as plates, profiles, injection molded articles, various work pieces, chips, granules, or foams, mainly two-dimensional bodies such as sheets, foils, lacquers, coatings, impregnations or mainly one-dimensional bodies such as threads, fibers, flocks, wires. Said materials may alternatively be present in a non-shaped state in various homogeneous or inhomogeneous distribution states, for example as powders, solutions, emulsions, dispersions, latices, pastes or waxes.

Fiber materials may be present as continuous filaments, stretched or unstretched, staple fibers, flocks, material in rope form, textile threads, yarns, twisted yarns, nonwovens, felts, laps, flocked articles or as textile fabrics or spun-bonded webs, knit fabrics or papers, card-boards or paper pastes.

The compounds to be used according to the invention are inter alia important for the treatment of textile organic materials, in particular textile fabrics. If fibers present as staple fibers or as continuous filaments in the form of ropes, fabrics, knit fabrics, non-wovens, flocked substrates or spun-bonded webs are to be optically brightened according to the invention, this is advantageously effected in an aqueous medium containing the corresponding compounds in a finely distributed form, as suspensions, so-called microdispersions, optionally solutions. Dispersion agents, stabilizers, cross-linking agents and further auxiliaries may be added in the treatment.

In dependence on the type of brightener used it may be advantageous to operate in a neutral, alkaline or acid bath. The treatment is generally peformed at a temperature of from about 20° to 140° C., for example at the boiling temperature of the bath or near the boiling temperature, at about 90° C. Solutions or emulsions in organic solvents may also be used for the finishing of textile substrates according to the invention, as is customary in dyeing practice in the so-called solvent dyeing (padding-thermofixation application, exhaustion process in dyeing machines).

The novel optical brighteners according to the present invention may be added to the materials prior to or during molding. In the manufacture of sheets or foils, for example, they may be incorporated into polyvinyl chloride by rolling at elevated temperature, or in the manufacture of shaped articles they may be added to the molding or to the injection molding compositions.

When fully synthetic or semi-synthetic organic materials are shaped by spinning processes or by means of spinning pastes, the optical brighteners may be applied according to the following methods:

addition to the starting substances, for example monomers, or to intermediates, for example precondensates, prepolymers, i.e. prior to or during polymerization, polycondensation or polyaddition, dusting onto polymer chips or granules for spinning pastes, bath dyeing of polymer chips or granules for spinning pastes, proportioned addition to spinning melts or spinning solutions, application onto tows prior to stretching.

The novel optical brighteners according to the invention may also be used in the following forms, for example:

(a) As mixtures with dyestuffs (tinting) or pigments (color pigments or in particular white pigments) or as addition to dyebaths, printing pastes, discharge or resist pastes, moreover for the aftertreatment of colorations, prints or discharge prints, (b) in admixture with so-called "carriers", wetting agents, softeners, swelling agents, antioxidants, light and heat stabilizers, chemical bleaching agents (chlorite bleaching, additives to bleaching baths), (c) in admixture with cross-linking agents or finishing agents, for example starch or synthetic finishing agents, or in combination with a great variety of textile finishing agents, in particular artificial resin finishes, for example, crease-resistant finishes such as "wash-and-wear", "permanent-press", "noiron", or flame-proof finishes, soft handle, anti-soiling, anti-static or anti-microbial finishes, (d) incorporation of the optical brighteners in polymer carrier materials, for example polymerization, polycondensation or polyaddition products, in dissolved or dispersed form for use in coating agents, impregnation agents or binding agents, for example as solutions, dispersions, emulsions, for textiles, nonwovens, paper, leather, (e) as additives to so-called "master batches", (f) as additives to a great variety of industrial products to bring them into a form that is easier marketable (for example for improving the appearance of soaps, detergents, pigments), (g) in combination with other optically brightening substances, (h) in spinning bath compositions, i.e. additives to spinning baths used for improving the lubricating properties for the processing of synthetic fibers, or in a special bath prior to stretching the fiber, (i) as scintillators for various purposes in the photographic field, for example for electrophotographic reproduction or supersensibilization, (j) in dependence on the substituents as laser dyestuffs.

When the brightening process is combined with textile treatment or finishing methods, corresponding resistant compositions are frequently used advantageously that contain the optically brightening compounds in a concentration sufficient to obtain the desired brightening effect.

In some cases the action of the brighteners may be improved by an after-treatment, for example a chemical acid treatment, a thermal treatment or a combined chemical/thermal treatment. Hence, when optically brightening a number of fiber substrates, for example polyester fibers, with the brighteners according to the invention, these fibers are advantageously impregnated with aqueous dispersions, optionally solutions, of the brighteners, at a temperature below 75° C., for example at room temperature, and subsequently subjected to a dry heat treatment, at a temperature above 100° C., these steps being advantageously preceded by drying the fibrous material at moderately elevated temperature, for example of at least 60° C. up to about 130° C. In this case the heat treatment in the dry state is advantageously carried out at a temperature between 120° and 225° C., for example by heating in a drying chamber, ironing the material at the temperature range indicated or by treating it with dry superheated steam. The drying and the dry heat treatment may follow each other immediately or be combined in a single step. When the compounds according to the invention are applied onto polyester fibers by one of the aforementioned application methods, excellent degrees of whiteness having a very high resistance to light are obtained.

The quantity of the novel optical brighteners according to the invention, calculated on the material to be brightened optically, may vary within wide limits. A distinct and durable effect may already be achieved with very small quantities, in some cases even with those of 0.001 weight %. Quantities of up to about 0.8 weight % and optionally up to about 2 weight % may be used alternatively, quantities between 0.005 and 2, preferably between 0.1 and 0.5 weight % being interesting for most practical purposes.

For various reasons the brighteners should frequently not be used as such, i.e. in the pure state, but in admixture with various auxiliaries or diluents such as anhydrous sodium sulfate, sodium sulfate decahydrate, sodium chloride, sodium carbonate, alkali metal phosphates, such as sodium or potassium orthophosphate, sodium or potassium pyrophosphate and sodium or potassium polyphosphates, or alkali metal silicates.

The novel optical brighteners are especially suitable as additives to washing baths or to industrial and household washing agents, wherein they are employed in various forms. They are suitably added to washing baths in the form of their solutions in water or in organic solvents or in finely divided state as aqueous dispersions. To household or industrial washing agents they are suitably added in whatever phase of the manufacture process, for example to the so-called "slurry" prior to atomization or they are added during the manufacture of liquid combinations of washing agents. They may be added either as solution or as dispersion in water or in another solvent or without auxiliaries as dry brightening powder. The brighteners may be mixed, kneaded or ground with the active detergents and be added in this form to the finished washing powder. Alternatively, they may be sprayed onto the ready washing powder in dissolved or in predispersed state.

Suitable washing agents are the known mixtures of active detergents such as soap in the form of chips and powders, synthetics, soluble salts of sulfonic acid semi-esters of higher fatty alcohols, of higher and/or multiple alkyl-substituted arylsulfonic acids, sulfocarboxylic acid esters of medium to higher alcohols, fatty acid acyl-aminoalkyl- or -aminoacrylglycerol sulfonates, phosporic acids esters of fatty alcohols etc. Suitable "builders" are in particular alkali metal poly- and -polymetaphosphates, alkali metal pyrophosphates, alkali metal salts of carboxymethyl-cellulose and other soil-redeposition inhibitors, further alkali metal silicates, alkali metal carbonates, alkali metal borates, alkali metal perborates, nitrilotriacetic acid, ethylene diamino-tetraacetic acid, foam stabilizers such as alkanolamides of higher fatty acids. The washing agents may further contain antistatic agents, refattening skin-protective agents such as lanolin, enzymes, antimicrobials, perfums and colorants.

The following examples illustrate the invention:

EXAMPLE 1

13.3 g of 4-(3-phenyl-1,3,4-oxadiazol-2-on-yl-(5)-benzylphosphinic acid diethyl ester (80.9% LGC) and 4.9 g of p-cyanobenzaldehyde (90%) are dissolved in 40 ml of dimethylformamide and dropped subsequently into a suspension of 1.9 g of potassium hydroxide in 40 ml of dimethylformamide (DMF), while maintaining a temperature of below 30° C. The reaction mixture is stirred for 3 hours, the precipitated reaction product is suction-filtered and washed neutral with methanol and water. Repeated redissolution from chlorobenzene gives 4.0 g of the compound 101 having a melting point of from 247° to 249° C. in the form of a slightly yellow crystal powder.

To prepare the above phosphonic acid ester 32.7 g of 4-(3-phenyl-1,3,4-oxadiazol-2-on-yl-(5))-benzyl bromide in 80 ml of DMF are heated with 18 ml of triethylphosphite to 145° to 150° C. for 3 hours. Subsequently, excess triethylphosphite and the solvent are distilled off in vacuo, leaving 39.4 g of a tough oil which is found to have a content of phosphonic acid ester of 80.9% by gaschromatography.

The above bromine compound is obtained by reacting 25.2 g of 4-(3-phenyl-1,3,4-oxadiazol-2-on-yl-(5))-toluene with 17.8 g of N-bromosuccinimide in 250 ml of tetrachloromethane at boiling temperature and in the presence of 0.1 g of azo-bis-isobutyronitril. Usual working up yields 32.7 g of the bromomethyl compound which after redissolution from ethanol exhibits a melting point of from 112° to 113° C.

The above toluene compound is obtained by reacting 113.2 g of toluylic acid phenyl hydrazide in 2 liters of toluene with 100 g of phosgene in the presence of 200 g of triethylamine. To this end, the solution of the hydrazide in toluene containing triethyl amine as proton scavenger, is heated to 90° to 100° C. and subsequently the specified quantity of phosgene is introduced into this solution, to make triethylamine hydrochloride precipitate. The reaction mixture is refluxed for 4 hours, supplemented with water and toluene is removed by steam distillation. The undissolved reaction product is suction-filtered and recrystallized from a mixture of 100 ml of DMF and 600 ml of methanol. 98.2 g of the oxadiazolone having a melting point of from 149° to 151° C. are obtained.

EXAMPLE 2

4,4'-Bis(3-phenyl-1,3,4-oxadiazol-2-on-yl-(5))-stilbene (106) is obtained in the following way: 8.0 g of 4-(3-phenyl-1,3,4-oxadiazol-2-on-yl-(5))-benzaldehyde and 13.3 g of 4-(3-phenyl-1,3,4-oxadiazol-2-on-yl-(5)-benzylphosphonic acid ester (cf. Example 1), dissolved in 40 ml of DMF, are added dropwise to a suspension of 1.9 g of potassium hydroxide in 40 ml of DMF at a temperature of from 20° and 30° C. The reaction mixture is stirred for 3 hours at room temperature, the precipitated reaction product is suction-filtered and washed neutral with methanol/water. A repeated redissolution from benzoic acid methyl ester with the addition of diatomaceous earth gives 4.0 g of the stilbene compound (106) having a melting point of from 297° to 299° C.

To prepare the above substituted benzaldehyde 33.1 g of 4-(3-phenyl-1,3,4-oxadiazol-2-on-yl-(5))-benzylbromide (cf. Example 1) in 200 ml of chloroform are refluxed for 2 hours with 14.0 g of urotropin. The resulting substance is suction-filtered after cooling to 0° to 5° C., washed with a little chloroform and refluxed with 150 ml of 50% acetic acid for 3 hours. The acetaldehyde formed is suction-filtered after having been stirred until cold at 5° C., subsequently is washed neutral with water and dried. 14.5 g of a colorless crystal powder having a melting point of from 148° to 149° C. are obtained.

EXAMPLE 3

The benzoxazole compound (111) is obtained in the following way:

A solution of 39.4 g of the phosphonic acid ester of Example 1 and of 22.3 g of the aldehyde of Example 2 in 200 ml of DMF is added dropwise to a suspension of 6.2 g of ground potassium hydroxide in 50 ml of DMF and the reaction temperature is maintained below 30° C. by cooling. The reaction product is stirred for 1 hour at room temperature, the precipitated reaction product is suction-filtered and washed twice with DMF and subsequently with water until neutral. Repeated redissolution from N-methyl pyrrolidone gives a light yellow crystal powder having a melting point of from 330° to 340° C.

The compounds listed in the following table are prepared in analogous manner.

$$Y-CH=CH-\underset{O}{\underset{\|}{\bigcirc}}\overset{N-N-R}{\underset{O}{\bigvee}}=O$$

| No | R | Y | M.p. | Adsorption > max (mμ) in DMF | Fluorine in DMF |
|----|---|---|------|------------------------------|-----------------|
| 101 | phenyl | —N=C—C6H4— | 247–249 | 352 | blue |
| 102 | phenyl | benzofuran-2-yl | 208–210 | 367 | blue |
| 103 | phenyl | benzoxazol-2-yl | 248–250 | 359 | blue |
| 104 | phenyl | 1-methylbenzimidazol-2-yl | 265–266 | 372 | greenish-blue |
| 105 | phenyl | 1,3-dimethylbenzimidazolium-2-yl (+) | 248–249 | 344 | blue |
| 106 | phenyl | 4-(3-phenyl-1,3,4-oxadiazol-2-on-5-yl)phenyl | 297–299 | 366 | blue |
| 107 | phenyl | 5-phenyl-1,3,4-oxadiazol-2-yl | 272–274 | 364 | violet |

-continued

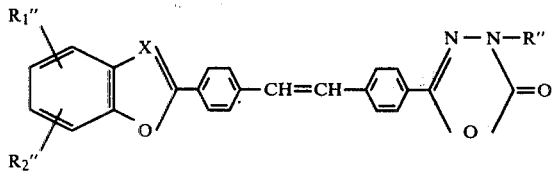

| No | R | Y | M.p. | Adsorption > max (mμ) in DMF | Fluorine in DMF |
|---|---|---|---|---|---|
| 108 | phenyl | (triazine-N-phenyl) | 236–239 | 353 | blue |
| 109 | phenyl | (triazinium CH₃, CH₃OSO₃⁻ phenyl) | 280–281 | 349 | blue |
| 110 | phenyl | (benzofuranyl-phenyl) | 261–264 | 378 | greenish-blue |
| 111 | phenyl | (benzoxazolyl-phenyl) | 330–340 | 370 | violet |

EXAMPLE 4

A fabric consisting of polyester staple fibers is impregnated with a 0.1% dispersion of the compounds (111) and subsequently squeezed off between rolls to a humidity content of 85%, calculated on the weight of the goods. After drying at 120° C. (20 seconds) it is thermosolated at 200° C. for 40 seconds on a tenter frame. The treated textile material exhibits an excellent degree of whiteness as compared to the untreated material.

Similarly good results are obtained when using the residual compounds listed in the table, in particular the compounds (106) and (107).

What is claimed is:

1. 1,3,4-Oxadiazolone-(2) compounds of the formula (1)

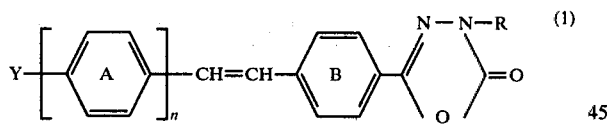

wherein

Y is phenyl, p-cyanophenyl, p-carbalkoxyphenyl, p-carboxyphenyl, cyano, carboalkoxy, carbonamide, 5-aryl-1,3,4-oxadiazolyl-(2), 3-aryl-1,3,4-oxadiazol-2-on-yl-(5), 1,2,4-triazolyl-(1), 1,2,3-triazolyl-(2), benzofuranyl-(2), benzoxazolyl-(2), benzimidazolyl-(2), 1,2,4-triazolium, benzimidazolium, N-methyl-benzimidiazolium or N-methyl-benzimidazolyl, R is hydrogen or alkyl which may be substituted by hydroxy, cyano, carboalkoxy, alkoxy, halogen, dialkylamino, trialkylammonium or R is phenyl which may be substituted by 1 to 3 alkyl, alkoxy, halogen or carboalkoxy.

2. 1,3,4-Oxadiazolone-(2) compounds as claimed in claim 1 of the formula $$\begin{array}{c} R_1'' \\ \diagdown \\ \diagup \\ R_2'' \end{array} \text{(benzofuran/benzoxazole)} - \text{C}_6\text{H}_4 - \text{CH}=\text{CH} - \text{C}_6\text{H}_4 - \text{C}(=\text{N}-\text{N}-\text{R}'') - \text{O} - \text{C}(=\text{O})$$

wherein

X is CH or N,

R" is hydrogen or alkyl which may be substituted by hydroxy, cyano, carboalkyl, alkoxy, halogen, dialkylamino, trialkylammonium or R" is phenyl which may be substituted by 1 to 3 alkyl, alkoxy, halogen or carboalkoxy, R"₁ and R"₂ when independent from one another have the same meaning as R" or are alkoxy, halogen, dialkylamino, trialkylammonium or R"₁ and R"₂ when taken together are dioxymethylene, dioxyethylene, alkylene or butadienylene.

* * * * *